United States Patent
Molin

(10) Patent No.: US 6,604,002 B2
(45) Date of Patent: Aug. 5, 2003

(54) MEASURING THE TRANS-VALVULAR BIO-IMPEDANCE IN AN ACTIVE IMPLANTABLE MEDICAL DEVICE, IN PARTICULAR A PACEMAKER, DEFIBRILLATOR AND/OR CARDIOVERTOR AND/OR MULTISITE DEVICE

(75) Inventor: Renzo Dal Molin, Chatillon (FR)

(73) Assignee: ELA Medical S.A., Montrouge (FR)

( * ) Notice: Subject to any disclaimer, the term of this patent is extended or adjusted under 35 U.S.C. 154(b) by 90 days.

(21) Appl. No.: 09/760,163

(22) Filed: Jan. 12, 2001

(65) Prior Publication Data

US 2001/0021864 A1 Sep. 13, 2001

(30) Foreign Application Priority Data

Jan. 14, 2000 (FR) .............................. 00 00482

(51) Int. Cl.[7] .......................... A61N 1/368; A61N 1/08; A61N 1/36; A61B 5/04
(52) U.S. Cl. .................... 607/28; 607/122; 600/508; 600/547
(58) Field of Search ..................... 607/28, 122, 123; 600/508, 547

(56) References Cited

U.S. PATENT DOCUMENTS

| | | | |
|---|---|---|---|
| 5,318,595 A | * 6/1994 | Ferek-Petric et al. ......... | 607/17 |
| 5,501,702 A | 3/1996 | Plicchi et al. ................. | 607/20 |
| 5,792,194 A | * 8/1998 | Morra .......................... | 607/17 |
| 6,278,894 B1 | * 8/2001 | Salo et al. .................... | 600/547 |

FOREIGN PATENT DOCUMENTS

| WO | 99/30777 | 12/1998 | .......... A61N/1/368 |
|---|---|---|---|

* cited by examiner

*Primary Examiner*—Carl Layno
(74) *Attorney, Agent, or Firm*—Orrick, Herrington & Sutcliffe LLP

(57) ABSTRACT

Measuring a trans-valvular bio-impedance in an active implantable medical device, in particular, a pacemaker, a defibrillator and/or a cardioverter and/or a multisite device in which electrodes are placed in at least one ventricular site and one atrial site and are connected to at least one circuit for the collection (detection) of cardiac signals, to detect a depolarization potential. The electrodes also are connected to a stimulation circuit to deliver stimulation pulses to at least some of the sites. The trans-valvular bio-impedance is measured by injecting a current between an atrial site and a ventricular site, and collecting a potential differential between an atrial site and a ventricular site. The measurement configuration is a tripolar configuration, with one site common to the injection and the collection, one site dedicated for the injection and one site dedicated for the collection.

16 Claims, 1 Drawing Sheet

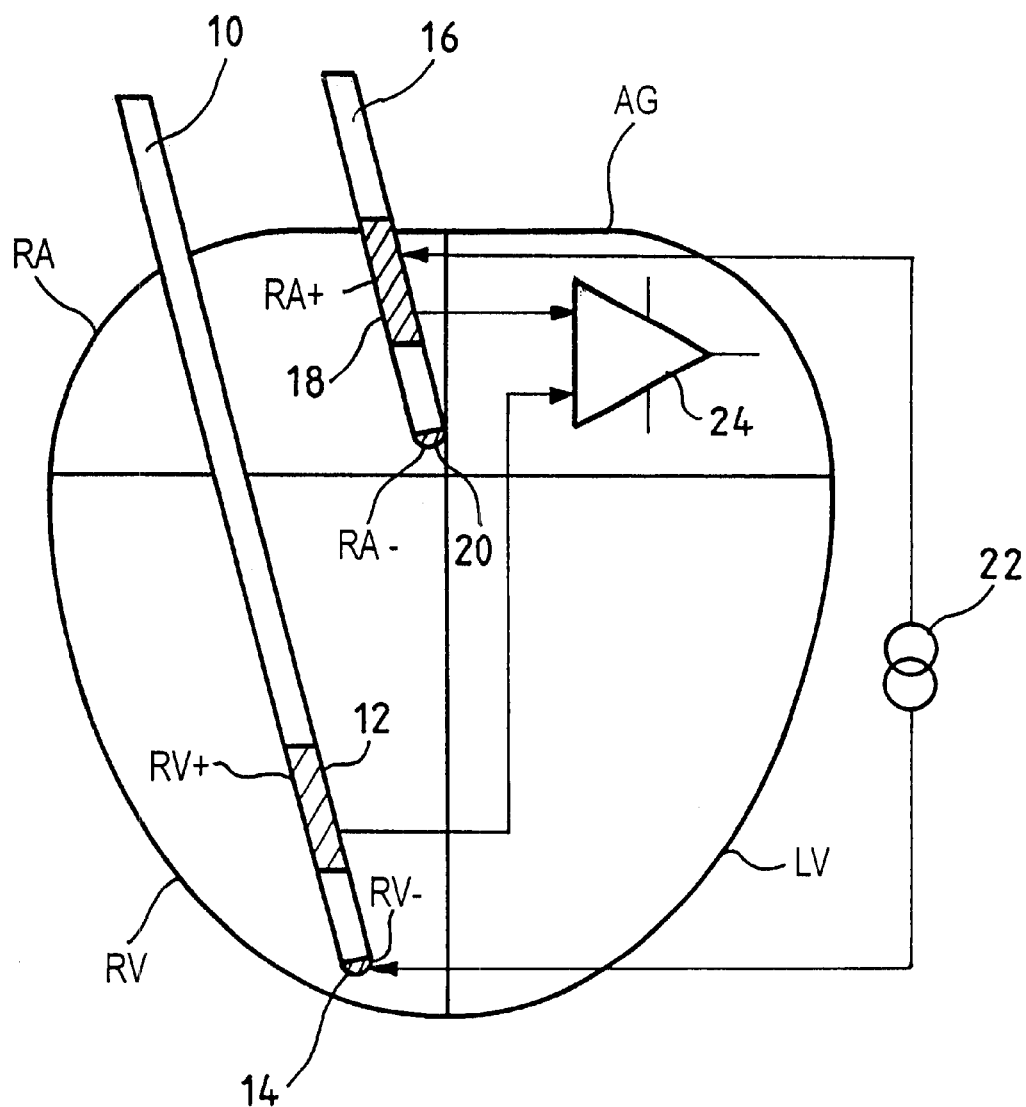

MEASURING THE TRANS-VALVULAR BIO-IMPEDANCE IN AN ACTIVE IMPLANTABLE MEDICAL DEVICE, IN PARTICULAR A PACEMAKER, DEFIBRILLATOR AND/OR CARDIOVERTOR AND/OR MULTISITE DEVICE

FIELD OF THE INVENTION

The present invention is directed to "active implantable medical devices" as such devices are defined by the Jun. 20, 1990 directive 90/385/CEE of the Council of the European Communities, more precisely to pacemaker, defibrillator and/or cardiovertor devices which are able to deliver to the heart pulses of low energy for the treatment of the cardiac rate disorders, and even more particularly, to the so-called "multisite" prostheses in which electrodes are placed in a plurality of distinct respective sites, comprising at least one ventricular site and one atrial site.

BACKGROUND OF THE INVENTION

Multisite prosthesis are known and include the following general types: "double chamber" (right atrial stimulation and right ventricular stimulation), "triple chamber" (right atrial stimulation and double ventricular stimulation), and "quadruple chamber" (double atrial stimulation and double ventricular stimulation).

The control of stimulation implies that there is a continuous adjustment of various parameters such as the stimulation frequency, the atrio-ventricular delay (AVD), or the inter-ventricular delay in the case of a bi-ventricular stimulation. These various parameters are adjusted according to signals delivered by sensors, for example, a measure of the well known minute-ventilation (MV), which is a cardiac parameter representative of the instantaneous metabolic needs of the patient.

Another parameter which is interesting to know is the cardiac flow. It can be particularly interesting with multisite-type pacemakers to obtain an indication of the cardiac flow, and thus of the ejection fraction, which is a well known hemodynamic reference parameter, in order to optimize stimulation of the various sites.

International patent application WO-A-99/34863 (assigned to Pacesetter AB) describes a lead allowing one to obtain an indication of this parameter by a measurement of the intracardiac pressure, using a piezoelectric sensor incorporated at the end of a lead. The pressure is integrated between the moment of opening and the moment of closing of the valve, which gives an indication of the work provided by the cardiac muscle. This information is then used, inter alia, to control the stimulation frequency and the atrio-ventricular delay. This manner of proceeding, however, if it is to be effective, requires a specific lead incorporating a piezoelectric sensor, as well as a particular electronic circuit to condition the signals produced by the piezoelectric sensor, to convert them and transmit them to the microprocessor of the pacemaker.

Another parameter which can be measured and correlated with the cardiac flow is the trans-valvular impedance, generally measured at the right heart. In this respect, Chirife U.S. Pat. No. 5,154,171 (Chirife) describes a manner of taking a dynamic measurement of bio-impedance, allowing one to evaluate the diastolic and systolic volumes, and to obtain therefrom an indication of the cardiac flow, and thus of the ejection fraction. The signal obtained is then used to control the heart rate so as to adjust the heart rate up or down in the direction that will obtain a maximization of the cardiac flow.

The Chirife patent proposes to make the bio-impedance measurement by injecting a current pulse between two points, and collecting (detecting) a differential potential between the same two points. In practice, however, it has been discovered that this configuration of injection/collection appears sensitive to the movement of the leads, and therefore does not allow a reliable and precise measurement of the trans-valvular impedance.

OBJECTS AND SUMMARY OF THE INVENTION

It is, therefore, an object of the present invention to overcome the aforementioned disadvantages by proposing a new measurement configuration for the trans-valvular impedance with a particular choice for the injection and collection sites.

Another object of the present invention is to use the parameter thus measured to control the inter-ventricular delay, in the case of a bi-ventricular stimulation (the trans-valvular impedance also being able of course to control the stimulation frequency and/or the atrio-ventricular delay).

The present invention is thus directed to an active implantable medical device, in particular a pacemaker, defibrillator and/or cardiovertor and/or a multisite device, in which electrodes are placed in a plurality of respective distinct sites comprising at least one ventricular site and one atrial site on the same side of the heart, these electrodes being connected to at least one circuit for the collection (detection) of cardiac signals, the collection circuit being able to detect depolarisation potentials including a differential potential between two electrodes, as well as to a stimulation circuit to apply stimulation pulses to at least certain ones of the aforesaid sites. This device further comprises means for evaluating the cardiac flow based upon a measurement of the trans-valvular bio-impedance, which means operates by injection of a current between an atrial site and a ventricular site, and the collection of a differential potential between an atrial site and a ventricular site.

According to the invention, a tripolar electrode configuration is used to obtain the trans-valvular bio-impedance, with one site common to the injection and the collection, one site dedicated to the injection, and one site dedicated to the collection. The common site is located in one of the cavities, and the two dedicated sites are located in the other cavity.

In a preferred embodiment, the device also comprises means for varying the inter-ventricular delay of the application of the respective stimulation pulses on the right and left ventricles (in the case of a multisite device), and/or means for varying the frequency of application of the stimulation pulses, and/or means for varying the atrio-ventricular delay in the application of the stimulation pulses. These various means, when employed independently or collectively, operate in response to the measured trans-valvular impedance to vary the control parameter in a direction that results in an improvement of the cardiac flow.

In one embodiment of the invention, the common site is an atrial site and the two dedicated sites are ventricular sites.

In another embodiment, the common site is a ventricular site and the two dedicated sites are atrial sites.

In yet another embodiment, the common site is a proximal electrode of a lead, and in yet another embodiment, the two dedicated sites are a proximal electrode and a distal electrode of the same lead, which may be an atrial site or a ventricular site.

In a preferred embodiment of the present invention, the site common to the injection and the collection is a proximal electrode of a right atrial lead, the site dedicated for the injection is a distal electrode of a right ventricular lead, and the site dedicated for the collection is a proximal electrode of the same right ventricular lead.

BRIEF DESCRIPTION OF THE DRAWING

Further features, characteristics and advantages of the present invention will appear to a person of ordinary skill in the art in view of the following detailed description, made with reference to the drawing annexed, which schematically represents a cardiac muscle with its four cavities: right atrium RA, left atrium LA, right ventricle RV, and left ventricle LV.

DETAILED DESCRIPTION OF THE INVENTION

With reference to the drawing, lead 10 is introduced into the right ventricle RV, with an annular proximal electrode 12, reference RV+, and a distal electrode at its extremity 14, reference RV−. A lead 16 is introduced into the right atrium RA, with an annular proximal electrode 18, reference RA+, and a distal electrode at its extremity 20, reference RA−.

If necessary, it can also be envisaged to introduce a lead on the left ventricle LV (not shown), for example, to allow a bi-ventricular stimulation (triple or quadruple chamber configuration) and/or to introduce a lead on the left atrium LA, if one wishes to carry out a collection of signals and/or a stimulation on two atriums (typically a quadruple chamber configuration).

The electrodes of the leads are connected to a case of the implantable device which includes various detection, stimulation and control circuits as are well known in the art, for example, a case of a multisite pacemaker such as that described in the EP-A-0 925 806 and the corresponding U.S. application Ser. No. 09/218,678 filed Dec. 22, 1998, which is commonly owned and co-pending, the disclosure of which is incorporated by reference herein in its entirety, and to which one will refer for further details. These detection, stimulation and control circuits form no part of the present invention in that any such circuit capable of performing the functions described herein may be used.

Among these circuits, it is envisaged to provide a circuit for measuring the trans-valvular bio-impedance (i.e., the impedance between right atrium RA and right ventricle RV). The measurement is classically carried out by injection of a pulse of current, schematized by the current generator 22, between two points, and by collection of a differential potential, schematised by the operational amplifier 24 between two points.

The injection and the collection of the signals in these various points can be carried out by a circuit such as that described in the Chirife U.S. Pat No. 5,154,171 above mentioned, or by a circuit such as that being used for measurement of the ventilation-minute (MV), as are known in the existing commercial devices such as, for example, the TALENT model family of pacemakers available from Ela Médical, Montrouge France, the assignee hereof. In this last case, the sites used to obtain an intracardiac injection/collection are different from the sites used to obtain the transpulmonary injection/collection (i.e., sites between heart and case) for measuring minute ventilation. In addition, the collection is operated at different frequency bands: such that, for example, a relatively low frequency is used for the measurement of MV, and a higher frequency is used for the measurement of trans-valvular impedance in accordance with the present invention. The current injected for the impedance measurement is, for example, a current of 40 $\mu$A, delivered in the form of a pulse of 5 $\mu$s width.

In other words, one of the advantages of the present invention is that it is possible to make use of the pre-existing measuring circuits and equipment used for traditional minute ventilation measurements, by recovering the measurement signal before the step of filtering the MV signal. This permits implementing an embodiment of the invention without a large additional cost of manufacture or design, or requiring additional space for additional measuring/signal conditioning circuits, which is critical in active implantable medical devices.

In the above mentioned Chirife U.S. Pat. No. 5,154,171, the points of injection and collection are the same ones (a bipolar configuration), while in the present invention the measurement configuration is a tripolar configuration, with one point common to the injection and to the collection.

Various configurations of injection and collection are thus possible.

The illustrated configuration, currently preferred, is injection between RA+ and RV−, and collection between RA+ and RV+. In other words, the common point, i.e., the reference for the measurement, is the proximal atrial electrode RA+.

The signal thus collected can be used to control the stimulation frequency, and/or the atrio-ventricular delay, and/or (and in a manner characteristic of the present invention) the inter-ventricular delay in the case of a bi-ventricular stimulation. The adjustment of these various parameters up or down is done of course in the direction of getting the maximum cardiac flow. This can be achieved by an incremental change process which is stopped when a maximum is detected, or which is reversed when a minimum flow level is obtained.

Other tripolar configurations of measurement are of course possible. For example, it is possible to reverse the roles of sites RV+ and RV−, i.e.: injection between RA+ and RV+, and collection between RA+ and RV−.

In the same way, it is possible to choose RA− instead of RA+ as the common site, i.e.: injection between RA− and RV−, and collection between RA− and RV+, or: injection between RA− and RV+, and collection between RA− and RV−.

It is also possible to reverse the role of the atrium and the ventricle, i.e., to choose as the common site a ventricular site. If one chooses RV+ as the common site, one will thus be able to have: injection between RV+ and RA−, and collection between RV+ and RA+.

It is also possible, in this last configuration, to switch the roles of RA+ and RA−, or to choose RV− instead of RV+ as the common site.

In addition, it should be understood that the embodiment that has just been described for the right heart (RA and RV cavities) is transposable to be used with the left heart (LV and LA cavities), although this choice involves a greater complexity and lower performance, due to the need to use coronary leads instead of intracardiac leads for the injection/collection.

One skilled in the art will appreciate that the present invention can be practiced by other than the described embodiments, which are presented for the purposes of illustration and not of limitation.

I claim:

1. An active implantable medical device, in particular a multisite device, in which electrodes are to be placed in a plurality of respective distinct sites comprising at least one ventricular site and one atrial site on the same side of the heart, these electrodes being connected to at least one circuit of collection of cardiac signals to detect a depolarization potential, and to a stimulation circuit to apply stimulation pulses to at least certain of the aforesaid sites, said device comprising:

(a) means for evaluating the cardiac flow by measurement of a trans-valvular bio-impedance, said means operating by injection of a current between an atrial site and a ventricular site, and collection of a differential potential between an atrial site and a ventricular site, wherein said measurement uses a tripolar configuration with one site common to the injection and the collection, one site dedicated for the injection, and one site dedicated for the collection, the common site being located in one of an atrial site and a ventricular site and the two dedicated sites being located in the other of the atrial site and the ventricular site; and (b) means for varying an inter-ventricular delay in the application of respective stimulation pulses to a right ventricle and a left ventricle, said means operating in response to the measured trans-valvular bio-impedance to vary said inter-ventricular delay in the direction of an improvement of cardiac flow.

2. The device of claim 1, wherein the common site is an atrial site and the two dedicated sites are ventricular sites.

3. The device of claim 1, wherein the common site is a ventricular site and the two dedicated sites are ventricular sites.

4. The device of claim 1, wherein the common site is a proximal electrode of a lead.

5. The device of claim 1, wherein the two dedicated sites are a proximal electrode and a distal electrode respectively of a lead.

6. The device of claim 1, wherein the site common to the injection and the collection is a proximal electrode of a right atrial lead, the site dedicated to the injection is a distal electrode of a right ventricular lead, and the site dedicated to the collection is a proximal electrode of said right ventricular lead.

7. An active implantable medical device, in particular a pacemaker, defibrillator and/or cardiovertor and/or a multi-site device, in which electrodes are to be placed in a plurality of respective distinct sites comprising at least one ventricular site and one atrial site on the same side of the heart, these electrodes being connected to at least one circuit of collection of cardiac signals to detect a depolarization potential, and to a stimulation circuit to apply stimulation pulses to at least certain of the aforesaid sites, said device comprising:

(a) means for evaluating the cardiac flow by measurement of a trans-valvular bio-impedance, said means operating by injection of a current between an atrial site and a ventricular site, and collection of a differential potential between an atrial site and a ventricular site, wherein said measurement uses a tripolar configuration with one site common to the injection and the collection, one site dedicated for the injection, and one site dedicated for the collection, the common site being located in one of an atrial site and a ventricular site and the two dedicated sites being located in the other of the atrial site and the ventricular site; and (b) means for varying an atrio-ventricular delay in the application of atrial and ventricular stimulation pulses, said means operating in response to the measured trans-valvular bio-impedance in the direction of the improvement of the cardiac flow.

8. The device of claim 7, wherein the common site is an atrial site and the two dedicated sites are ventricular sites.

9. The device of claim 7, wherein the common site is a ventricular site and the two dedicated sites are ventricular sites.

10. The device of claim 7, wherein the common site is a proximal electrode of a lead.

11. The device of claim 7, wherein the two dedicated sites are a proximal electrode and a distal electrode respectively of a lead.

12. The device of claim 7, wherein the site common to the injection and the collection is a proximal electrode of a right atrial lead, the site dedicated to the injection is a distal electrode of a right ventricular lead, and the site dedicated to the collection is a proximal electrode of said right ventricular lead.

13. An active implantable medical device, in particular a pacemaker, defibrillator and/or cardiovertor and/or a multi-site device, in which electrodes are to be placed in a plurality of respective distinct sites comprising at least one ventricular site and one atrial site on the same side of the heart, these electrodes being connected to at least one circuit of collection of cardiac signals to detect a depolarization potential, and to a stimulation circuit to apply stimulation pulses to at least certain of the aforesaid sites, said device comprising:

(a) means for evaluating the cardiac flow by measurement of a trans-valvular bio-impedance, said means operating by injection of a current between an atrial site and a ventricular site, and collection of a differential potential between an atrial site and a ventricular site, wherein said measurement uses a tripolar configuration with one site common to the injection and the collection, one site dedicated for the injection, and one site dedicated for the collection, wherein the common site is an atrial site and the two dedicated sites are ventricular sites; and (b) means for varying a stimulation pulse frequency, said means operating in response to the measured trans-valvular bio-impedance to vary said frequency in a direction of an improvement of cardiac flow.

14. An active implantable medical device, in particular a pacemaker, defibrillator and/or cardiovertor and/or a multi-site device, in which electrodes are to be placed in a plurality of respective distinct sites comprising at least one ventricular site and one atrial site on the same side of the heart, these electrodes being connected to at least one circuit of collection of cardiac signals to detect a depolarization potential, and to a stimulation circuit to apply stimulation pulses to at least certain of the aforesaid sites, said device comprising:

(a) means for evaluating the cardiac flow by measurement of a trans-valvular bio-impedance, said means operating by injection of a current between an atrial site and a ventricular site, and collection of a differential potential between an atrial site and a ventricular site, wherein said measurement uses a tripolar configuration with one site common to the injection and the collection, one site dedicated for the injection, and one site dedicated for the collection, wherein the common site is a ventricular site and the two dedicated sites are ventricular sites and (b) means for varying a stimulation pulse frequency, said means operating in response to the measured trans-valvular bio-impedance to vary said frequency in a direction of an improvement of cardiac flow.

15. An active implantable medical device, in particular a pacemaker, defibrillator and/or cardiovertor and/or a multi-site device, in which electrodes are to be placed in a plurality of respective distinct sites comprising at least one ventricular site and one atrial site on the same side of the heart, these electrodes being connected to at least one circuit of collection of cardiac signals to detect a depolarization potential, and to a stimulation circuit to apply stimulation pulses to at least certain of the aforesaid sites, said device comprising:

(a) means for evaluating the cardiac flow by measurement of a trans-valvular bio-impedance, said means operating by injection of a current between an atrial site and a ventricular site, and collection of a differential potential between an atrial site and a ventricular site, wherein said measurement uses a tripolar configuration with one site common to the injection and the collection, one site dedicated for the injection, and one site dedicated for the collection, the common site being a proximal electrode of a lead and located in one of an atrial site and a ventricular site and the two dedicated sites being located in the other of the atrial site and the ventricular site; and (b) means for varying a stimulation pulse frequency, said means operating in response to the measured trans-valvular bio-impedance to vary said frequency in a direction of an improvement of cardiac flow.

16. The device of claim 15 wherein the common site is a proximal electrode of a right atrial lead, the site dedicated to the injection is a distal electrode of a right ventricular lead, and the site dedicated to the collection is a proximal electrode of said right ventricular lead.

* * * * *